(12) United States Patent
Engman (10) Patent No.: US 9,522,051 B2
(45) Date of Patent: Dec. 20, 2016

(54) SPACER ELEMENT

(75) Inventor: Fredrik Nils Engman, Molnlycke (SE)

(73) Assignee: Neoss Limited, Harrogate (GB)

( * ) Notice: Subject to any disclaimer, the term of this patent is extended or adjusted under 35 U.S.C. 154(b) by 0 days.

(21) Appl. No.: 12/988,505

(22) PCT Filed: Apr. 17, 2009

(86) PCT No.: PCT/GB2009/050388
§ 371 (c)(1),
(2), (4) Date: Dec. 3, 2010

(87) PCT Pub. No.: WO2009/127880
PCT Pub. Date: Oct. 22, 2009

(65) Prior Publication Data
US 2011/0097687 A1    Apr. 28, 2011

(30) Foreign Application Priority Data
Apr. 18, 2008   (GB) .................... 0807118.5

(51) Int. Cl.
*A61C 8/00*   (2006.01)
(52) U.S. Cl.
CPC .................... *A61C 8/005* (2013.01)
(58) Field of Classification Search
CPC ............. A61C 8/005; A61C 8/00
USPC ............. 433/172–174, 201.1
See application file for complete search history.

(56) References Cited

U.S. PATENT DOCUMENTS

| | | | |
|---|---|---|---|
| 5,026,285 A | 6/1991 | Durr et al. | |
| 5,116,225 A * | 5/1992 | Riera | A61C 8/005 433/173 |
| 5,125,840 A | 6/1992 | Durr et al. | |
| 5,195,891 A * | 3/1993 | Sulc | 433/173 |
| 5,368,483 A | 11/1994 | Sutter et al. | |
| 5,947,733 A | 9/1999 | Sutter et al. | |
| 6,227,859 B1 * | 5/2001 | Sutter | 433/173 |
| 6,332,777 B1 | 12/2001 | Sutter | |
| 6,461,160 B1 | 10/2002 | Sutter | |
| 6,663,388 B1 | 12/2003 | Schär et al. | |
| 6,848,908 B2 | 2/2005 | Björn et al. | |
| 7,300,283 B2 | 11/2007 | Aravena et al. | |
| 2004/0005530 A1 | 1/2004 | Mullaly et al. | |

(Continued)

FOREIGN PATENT DOCUMENTS

| | | |
|---|---|---|
| DE | 19609174 A1 | 9/1996 |
| FR | 2745998 A1 | 9/1997 |

(Continued)

OTHER PUBLICATIONS

ISA European Patent Office, International Search Report of PCT/GB2009/050388, Jul. 23, 2009, 6 pages.

(Continued)

*Primary Examiner* — Cris L Rodriguez
*Assistant Examiner* — Mirayda A Aponte
(74) *Attorney, Agent, or Firm* — Alleman Hall McCoy Russell & Tuttle LLP (57) ABSTRACT

Various embodiments for a spacer element that may be used in a dental implant assembly are described. In one example, the spacer element has a single aperture therethrough. Further, the single aperture includes an implant screw access bore and an offset abutment screw bore, longitudinal axes of which intersect within the single aperture.

24 Claims, 10 Drawing Sheets

(56) References Cited

U.S. PATENT DOCUMENTS

2004/0243126 A1* 12/2004 Carbone et al. ............... 606/61
2005/0065525 A1   3/2005 Aringskog et al.
2011/0097687 A1   4/2011 Engman

FOREIGN PATENT DOCUMENTS

| WO | 9714371 | 4/1997 |
| WO | 9852488 | 11/1998 |
| WO | 2004032786 A1 | 4/2004 |
| WO | 2007078137 A1 | 7/2007 |
| WO | WO 2007078137 A1 * | 7/2007 |
| WO | 2008002065 A1 | 1/2008 |

OTHER PUBLICATIONS

ISA European Patent Office, International Search Report of PCT/GB2009/050382, Sep. 9, 2009, 5 pages.
Engman, Fredrik Nils, "Locking Ring," U.S. Appl. No. 12/988,503, filed Dec. 3, 2010, 13 pages.

* cited by examiner

SPACER ELEMENT

FIELD OF THE INVENTION

The present invention relates to the field of a novel spacer element for use in connection with a dental implant assembly and particularly a spacer element for use with an angulated or inclined abutment.

The present invention also relates to the field of a dental implant assembly comprising such a novel spacer element and to an implant screw pre-mounted in such a spacer element. Furthermore the invention relates to the field of a novel dental construction e.g., a dental bridge comprising one or more spacer elements and to methods related thereto.

BACKGROUND

In a dental implant assembly, there is usually a fixing of some kind for fixing, inter alia, an abutment or a spacer element to a dental implant. Typically, the fixing is a screw known as an implant screw. This implant screw is not the same as the implant per se which is itself externally threaded.

It is often desirable to have the abutment positioned at an inclined angle relative to (i.e., not coaxial with) the implant screw or implant per se. This may be of value in a number of different circumstances, however, it is especially advantageous when used in connection with dental bridges and the like. It is often desirable to design a dental bridge or superstructure with an angled implant screw channel so that, inter alia, the mouth of the channel can be on the interior or the occlusal surface of the dental bridge.

However, the provision of an inclined abutment (angulated relative to the implant screw and thereby the implant) is problematical since it makes it difficult or impossible to easily access the head of the implant screw with the usual (substantially straight) tool through the angulated abutment bore. There have been a number of attempts to try to overcome this problem.

For example, U.S. Pat. No. 6,663,388 to Straumann describes a two part dental implant comprising a straight or angular abutment which can be established by means of a base screw and a supporting ring. The abutment is provided with an inlet in the form of an axial passage. From the side of the root part, a base screw is pushed with its screw head first into the axial passage. The threaded shank of the base screw, when inserted, protrudes from the root part of the abutment. The protruding portion is intended for engagement in the axial internally threaded hole in the implant. Thus, after insertion of the base screw into the abutment, a support ring is pushed over the threaded shank of the base screw into the mouth of the inlet and is fixed in its intended position. Fixing takes place by radial welding to the lower edge of the abutment.

U.S. Pat. No. 6,848,908 to Nobel Biocare describes a dental implant arrangement, comprising a spacer element provided with a first passage having a centre line and an opening to receive a screw adapted to be fastened in an implant and being capable of receiving a screwdriver, and a second passage having an opening and a centre line along a longitudinal axis arranged at an angle with respect to a direction of screwing, the first passage being arranged at an angle relative to a direction of screwing of the first screw. The second passage is adapted to receive a second screw and a corresponding screwdriver, the second screw being there to fasten the superstructure to the spacer; wherein the centre lines angled with respect to the direction of screwing.

We provide a novel spacer element and corresponding dental implant assembly which overcomes or mitigates the disadvantages of and/or differs from the prior art assemblies.

STATEMENT OF INVENTION

Therefore, according to one embodiment of the invention, there is provided a spacer element for use in a dental implant assembly having a single aperture therethrough, the single aperture comprising an implant screw access bore and an offset abutment screw bore.

Preferably, the longitudinal axes of the implant screw access bore and the offset abutment screw bore, when projected (for example onto a plane extending substantially vertically through said single aperture), intersect within said single aperture.

More particularly, the implant screw access bore is designed such that, in use, the implant screw access bore is substantially coaxial with the implant screw. However, it will be understood that the implant screw access bore may be inclined relative to the implant or the implant screw. The degree of incline at which the implant screw access bore is inclined relative to the implant or the implant screw may vary, but preferably may be from 0 to 10 degrees. The implant screw access bore is preferably threadless or substantially threadless, although it will be understood that the screw access bore may still coincide with a thread. Such an arrangement is advantageous in that, inter alia, the dental practitioner is provided with unhindered access to the implant screw.

Although part of the single aperture, the abutment screw bore is offset, angulated or inclined from the coaxial implant screw access bore and the implant screw. The degree of offset may vary. Thus, depending upon, inter alia, the nature of the implant or construction which is being designed, the angulation of the abutment, the offset may be from 1 to 30 degrees, preferably 15 to 30 degrees, when measured relative to the longitudinal axis of the implant screw access bore. However, as hereinbefore described, the implant screw access bore may itself be inclined relative to the implant or the implant screw. Thus, in use, the abutment may be positioned at an angle relative to the implant screw, this angle ranging from 1 to 40 degrees, with a subsequent angulation between the implant and abutment connecting surfaces of the spacer. The abutment screw bore is threaded to facilitate engagement with the abutment. Preferably the thread is cut outwardly into the wall of the abutment screw bore so as not to impede the access into the implant screw access bore. The angulated abutment may find utility in a dental implant assembly or in a dental construction or dental bridge.

In one embodiment of the invention there is provided a spacer element comprising a threadless bore and an offset threaded bore. Preferably, the spacer element comprises a threadless implant screw access bore and an offset threaded abutment bore. Preferably, the threadless aperture is substantially coaxial with the implant screw, with the means of engaging an implant screw and the threaded aperture offset. Thus, in this embodiment the threadless bore will essentially bisect the threaded bore. Therefore, the threaded bore will comprise a bore that is only partially threaded. The amount of thread will vary depending, inter alia, upon the angulation of the offset aperture, size of thread, type of thread and size of implant screw access bore. Thus, there is also provided a spacer element comprising single aperture which is provided with a threadless bore and an offset partially threaded bore. Preferably, the partially threaded bore is offset from the axis of the implant or implant screw, e.g., offset by 1 to 30 degrees. Thus, the threadless bore is preferably coaxial with the implant or implant screw or is only marginally offset, e.g., offset by from 0 to 10 degrees.

Preferably, the spacer element is provided with an implant screw engaging portion or implant engaging portion and an abutment screw engaging portion. Such engaging portions may comprise conventional engaging mechanisms known per se, such as internal or external connection arrangements, for example, internal or external versions of a hex or morse taper; and combinations thereof including means to provide options for rotational or non-rotational engagement. Alternatively, the engaging mechanism may comprise a screw, for example, which may be dropped through the spacer such that it is positioned to engage the implant. When the engaging mechanism comprises a drop through screw as hereinbefore described, the spacer element may advantageously be provided with an internal flange against which the "drop through" screw may rest. In a further alternative, the spacer element may be provided with a locking ring. The locking ring may be adapted to engage with an implant and/or an implant screw. It is desirable that the locking ring is integral to the spacer element. Alternatively, the locking ring may be fixed onto the spacer element, e.g., by welding. The locking ring may be provided with one or more longitudinal slots in the circumferential wall of the locking ring. Thus, the locking ring may comprise a resilient material, such as a plastic or metal, so that in use, the one or more longitudinal slots will allow an expansion of the locking ring enabling it to be pushed into position onto, for example, an implant screw being positioned by other means then dropped through as previously described.

In most cases, a dental implant is provided with a blind bore for engagement with the implant screw. In addition the implant can provide an annular recess for housing the head of the implant screw. Thus, in a further preferred embodiment of the invention the locking ring is dimensioned such that it will form a snug fit within the annular recess of the implant.

Alternatively, the locking ring may have a diameter which is less than that of the annular recess of the implant screw. Such an arrangement facilitates the insertion of the locking ring into the recess. However, preferably the outer wall of the cylindrical body may be provided with means of engaging with the annular recess. Preferably, such means is adapted to engage the internal wall of the annular recess of the implant. Although a variety of such means may be used, a simple engaging means may comprise providing the outer wall of the locking ring with a boss, protruding from the wall, preferably, the boss comprises a circumferential ridge, although it will be understood by the person skilled in the art that such a ridge may be continuous or non-continuous.

The spacer element of the invention may be advantageously included in a dental implant assembly. Therefore, in another embodiment there is provided a dental implant assembly comprising a spacer element as hereinbefore described, a dental implant and/or a dental abutment as hereinbefore described. Thus, the spacer element may be pre-mounted on an implant or an implant screw as hereinbefore described.

Furthermore, the abutment may be a conventional abutment used in an implant assembly or a dental construction such as a dental bridge. Thus, the abutment will be provided with an axial bore, said bore being arranged to receive an abutment screw to be attached to the spacer.

The assembly of the invention may also be provided in kit form. Therefore, in one embodiment we provide a kit comprising a spacer element as hereinbefore described and one or more of a driving tool, a dental implant, a dental abutment, implant screw and abutment screw. Preferably the kit of the invention comprises at least a spacer element, a dental implant and a dental abutment, and optionally a driving tool.

In another embodiment of the invention there is provided a method of producing a dental implant assembly which comprises at least an implant screw; arranged in a spacer element as hereinbefore described; and locating an implant abutment in or on the spacer element.

There is further provided a method of anchoring an implant abutment to an implant which comprises at least positioning a spacer already equipped with an implant screw on the implant and locating an implant abutment in or on the spacer element.

In the anchoring method as hereinbefore described, the method may comprise anchoring in a patient or, alternatively, anchoring in a dental bridge or dental construction.

Furthermore, a dental bridge or dental construction comprising the implant assembly of the invention is novel per se. Therefore, according to an additional embodiment of the invention we provide a dental bridge or dental construction comprising one or more dental implant assemblies as hereinbefore described.

BRIEF DESCRIPTION OF THE FIGURES

The invention will now be exemplified in certain embodiments with reference to the following drawings.

FIG. 9b shows a cross-sectional view of the assembly shown in FIG. 9a.

DETAILED DESCRIPTION

Throughout the description and claims of this specification, the words "comprise" and "contain" and variations of the words, for example, "comprising" and "comprises,"

means "including but not limited to," and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds or groups described in conjunction with a particular aspect, embodiment or example of the invention are to be understood to be applicable to any other aspect, embodiment or example described herein unless incompatible therewith.

Throughout the description and claims of this specification, the terms "aperture" and "bore" include without limitation any aperture, opening, bore, channel, passage or the like.

Throughout the description and claims of this specification, the terms "inclined", "angulated" and "offset" may be used interchangeably to refer to a component whose longitudinal axis, in use, is not coaxial with the longitudinal axis of another component (for example, a dental implant) with which the first component is to be used.

Referring to FIGS. 1a to c and 2, a spacer element 1 comprises an implant facing surface 2 with a circumferential side outer wall 3 and an abutment facing surface 4. The spacer may be made of any suitable material, in particular, titanium or titanium alloy. The spacer element is provided with a single aperture 5 therethrough. The height of the circumferential side wall 3 varies around the circumference of the spacer element 1 such that the abutment facing surface 4 is inclined with respect to the implant facing surface 2.

The single aperture 5 has two portions, firstly an implant screw access bore 6 with side wall 7 and secondly an abutment screw bore 8 with side wall 9. The side wall 7 of the implant screw access bore 6 comprises a smooth inner surface and the side wall 9 of the abutment screw bore 8 comprises an inner threaded surface 10.

The aperture 5 defines a passage via which the implant screw is accessible and via which a substantially linear tool may be inserted to engage and turn the implant screw to secure it to an implant. The opening of the aperture 5 is substantially circular, but may include a notch or cut-away portion 11 therein to facilitate insertion of a tool.

It can be seen that the implant screw access bore 6 has a substantially smooth side wall 7 and the abutment screw bore 8 has an at least partially-threaded side wall 9.

Figure 1A:
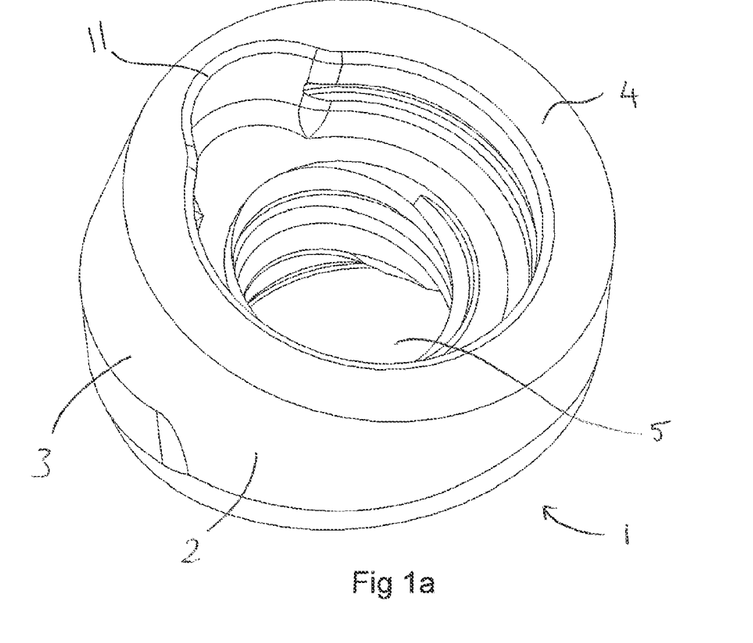
FIGS. 1a to c show perspective views of the spacer element of one embodiment of the invention.
Figure 1B:
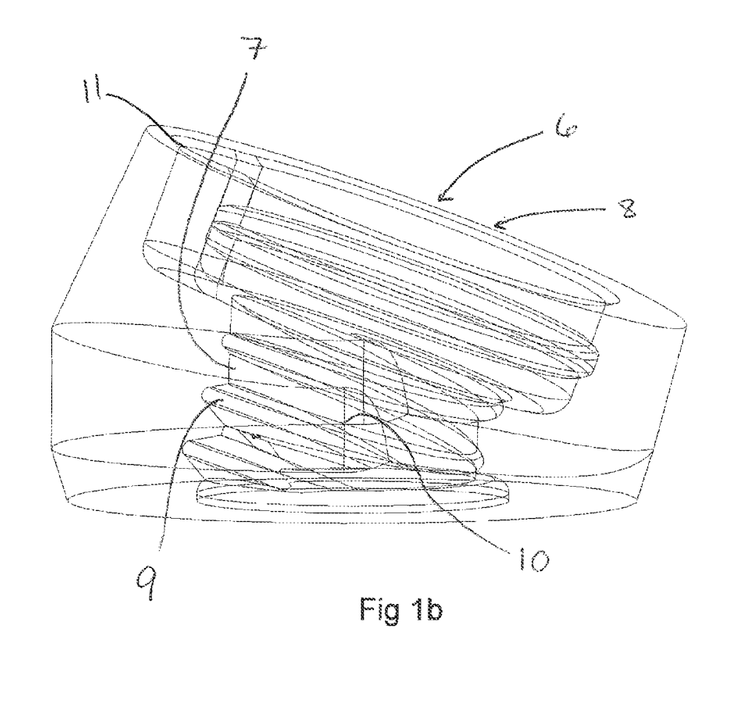
Figure 1C:
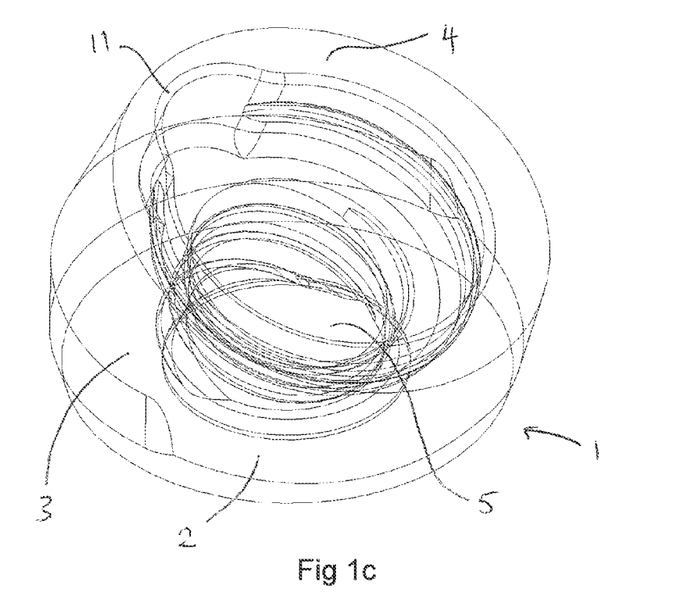
Figure 2:
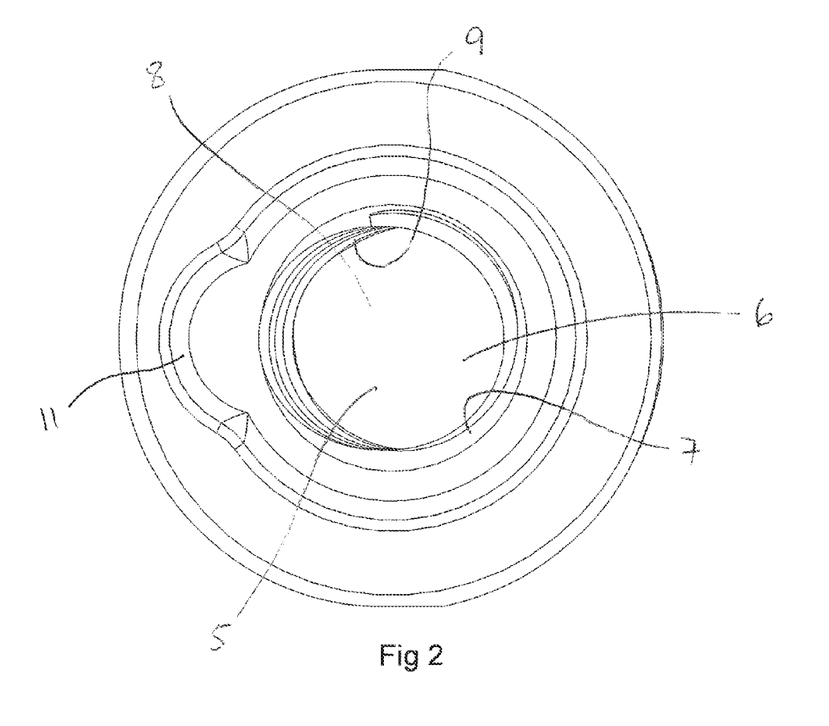
FIG. 2 shows a plan view of the spacer element of the spacer shown in FIGS. 1a to c.
Figure 3A:
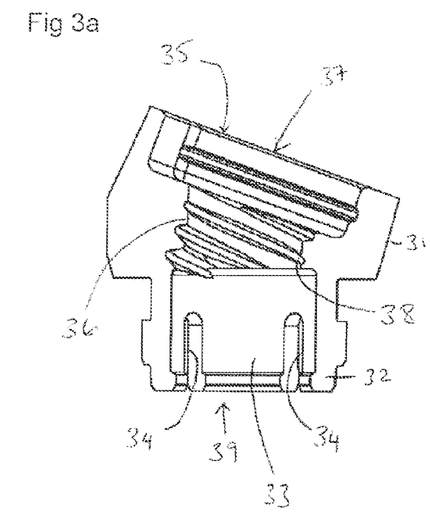
FIGS. 3a to b show cut away views of two alternative embodiments of the spacer element of the invention.
Figure 3B:
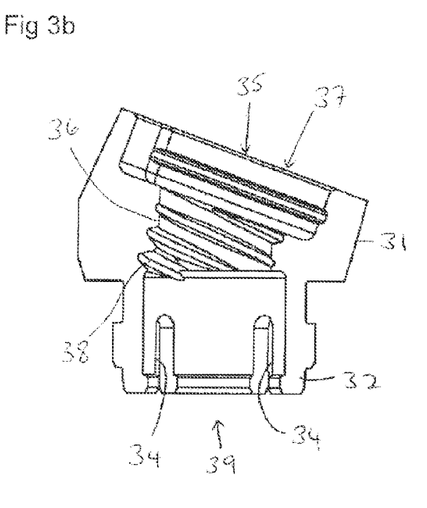

Referring to FIGS. 3a and 3b, the spacer element 31 includes means to connect to an implant engaging portion such as an integral locking ring 32 adapted to engage with an implant screw (not shown). The locking ring 32 is provided with longitudinal slots 34 cutting into an annular side wall 33. The spacer element 32 is provided with an implant screw access bore 35 with an internal side wall 36 and an abutment screw bore 37 with an internal side wall 38. FIG. 3a illustrates an abutment screw bore 37 with an incline angle of 20°, relative to the implant screw bore (39) and FIG. 3b illustrates an abutment screw bore 37 with an incline angle of 30°, relative to the implant screw bore (39). If viewed alone the implant screw access bore 35 would have a smooth, i.e., threadless, internal side wall 36. Similarly, if viewed alone, abutment screw bore 37 would have a threaded internal side wall 38. In the illustrated spacer element the implant screw access bore 35 and the abutment screw bore 37 overlap or interfere with one another.

Figure 4A:
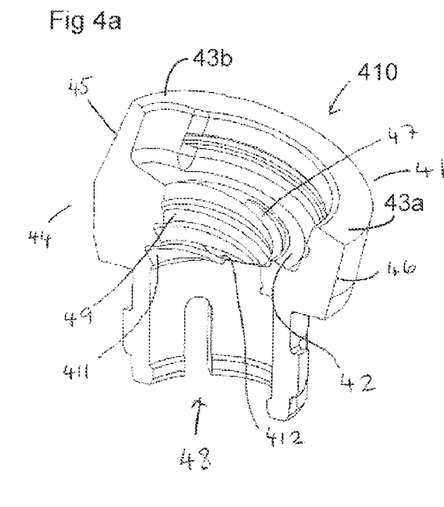
FIGS. 4a to b show cut away perspective views of the spacer element shown in FIGS. 3a to b respectively.
Figure 4B:
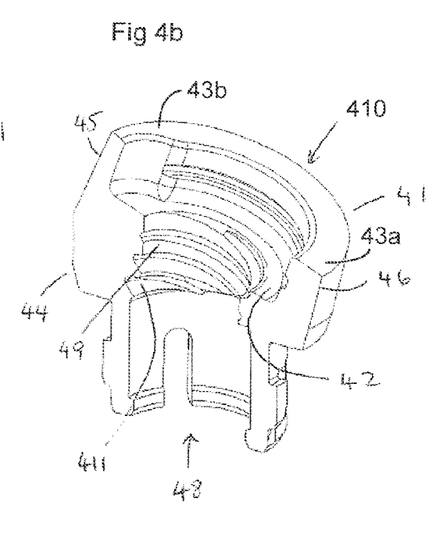

Referring to FIGS. 4a and 4b, the spacer element 41 is provided with an internal connection 42 which is adapted to act as a seat or holder for an abutment (not shown). It will be understood that the connection may optionally be external. In order for the abutment facing surface 43a to be inclined to 43b, the outer wall 44 of the spacer element 41 exhibits a corresponding change in height as the space difference between 43a and 43b. Thus, in the embodiment illustrated, the wall 44 of the spacer element 41 essentially comprises a high region 45 gradually reducing to a low 46 region. The internal portion 47 of the spacer implant 41 comprises an implant screw head access bore 48 provided with side wall 49, and an abutment screw bore 410 with side wall 411. If viewed alone the implant screw access bore 48 would have a smooth, i.e., threadless, internal side wall 49. Similarly, if viewed alone, abutment screw bore 410 would have a threaded internal side wall 411. In the spacer element of the invention the implant screw access bore 48 and the abutment screw bore 410 overlap or interfere with one another.

The thread 412 is cut outwardly from the wall 411 so as not to impede the access into the implant screw access bore 48 from the abutment surface 43a direction.

It will be appreciated by the person skilled in the art that the number of thread turns may vary, but in the embodiment shown, may include two or three threads whereas the low side may comprise only a single thread.

Figure 5:
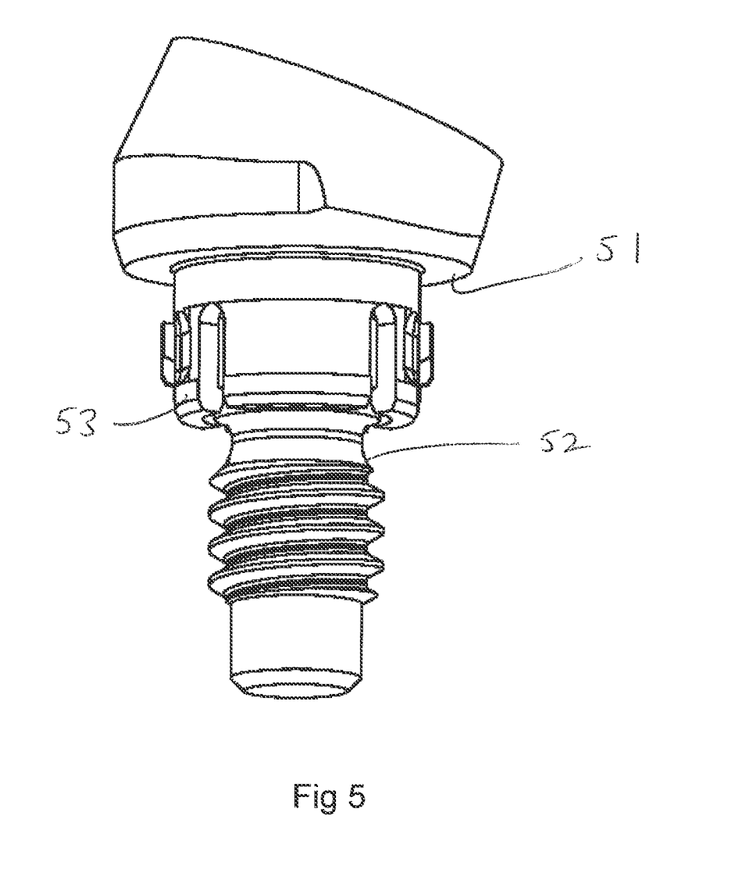
FIG. 5 shows a perspective view of an assembly that comprises the spacer element of FIG. 3a attached to an implant screw.

Referring to FIG. 5 the spacer element 51 is located on an implant screw 52 by way of an integral locking ring 53 prior to fitting into a patient with subsequent connection to a dental restoration, such as a prefabricated dental bridge (not shown).

Figure 6:
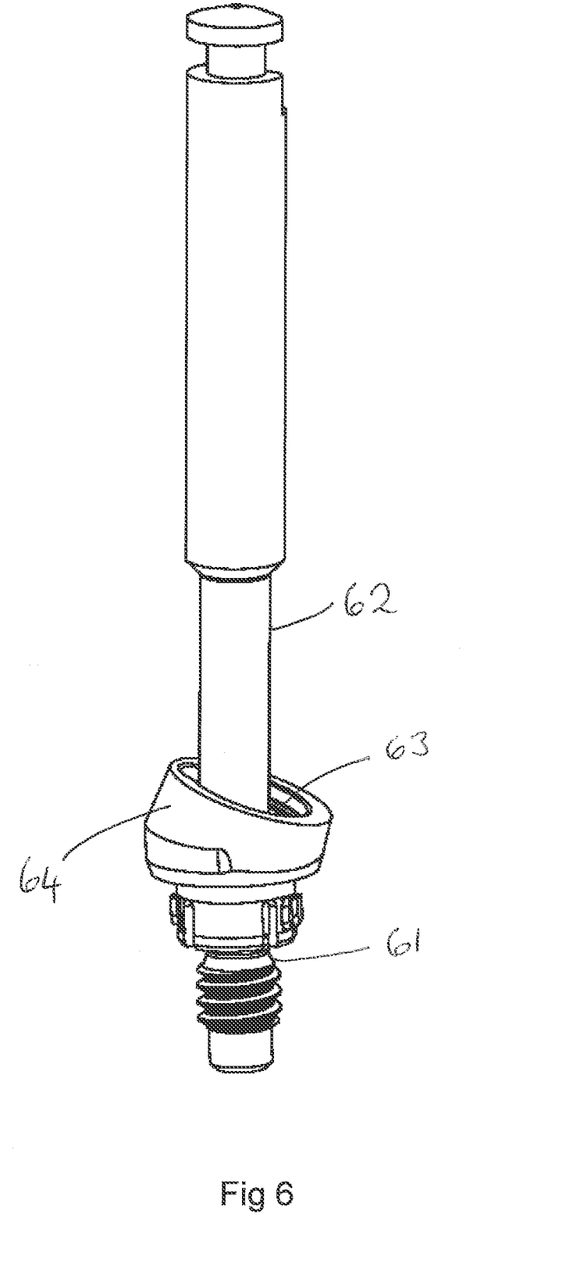
FIG. 6 shows a perspective view of the spacer element and implant screw assembly shown in FIG. 5 in use with a screwdriver in the screw access bore.

Referring to FIG. 6, in use, the spacer 64 may be screwed into position by the use of a conventional dental screwdriver 62 or other driving tool using the implant screw 61. The substantially linear screwdriver 62 or driving tool passes through the implant screw access bore 63 of the spacer element 64.

Figure 7A:
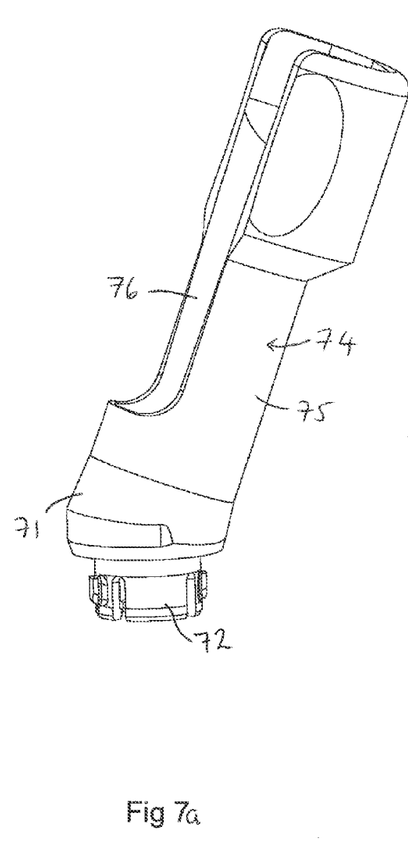
FIG. 7a shows a perspective view of a spacer element fitted with a holder and FIG. 7b shows a cross-sectional view thereof.
Figure 7B:
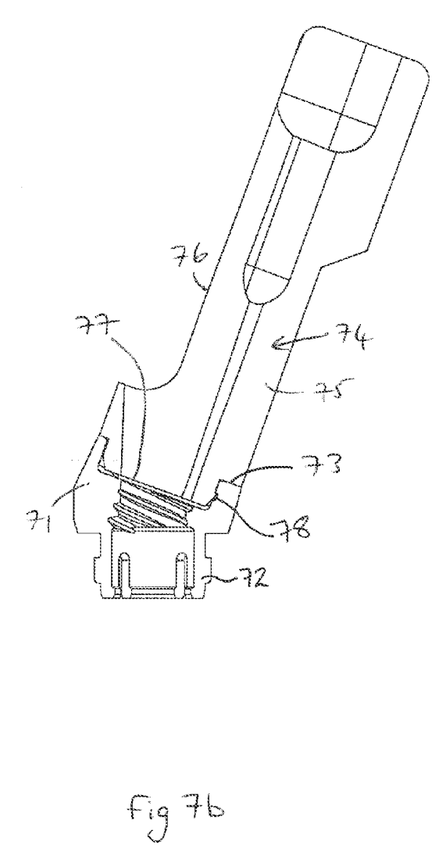

Referring to FIGS. 7a and 7b, a spacer element 71 is provided with an integral locking ring 72. An upper surface 73 of the spacer element 71 is provided with a handle 74. The handle 74 comprises a longitudinal substantially cylindrical body 75. One side of the cylindrical body 75 has a cut-away portion 76, such that, in situ, the cut-away portion 76 provides access to the bore(s) 77 of the spacer element 71. The handle 74 may be pre-mounted through means like the groove 78 on the spacer element 71 (into which the handle can snap-fit) and is used to carry and position the spacer element onto the implant.

Figure 8:
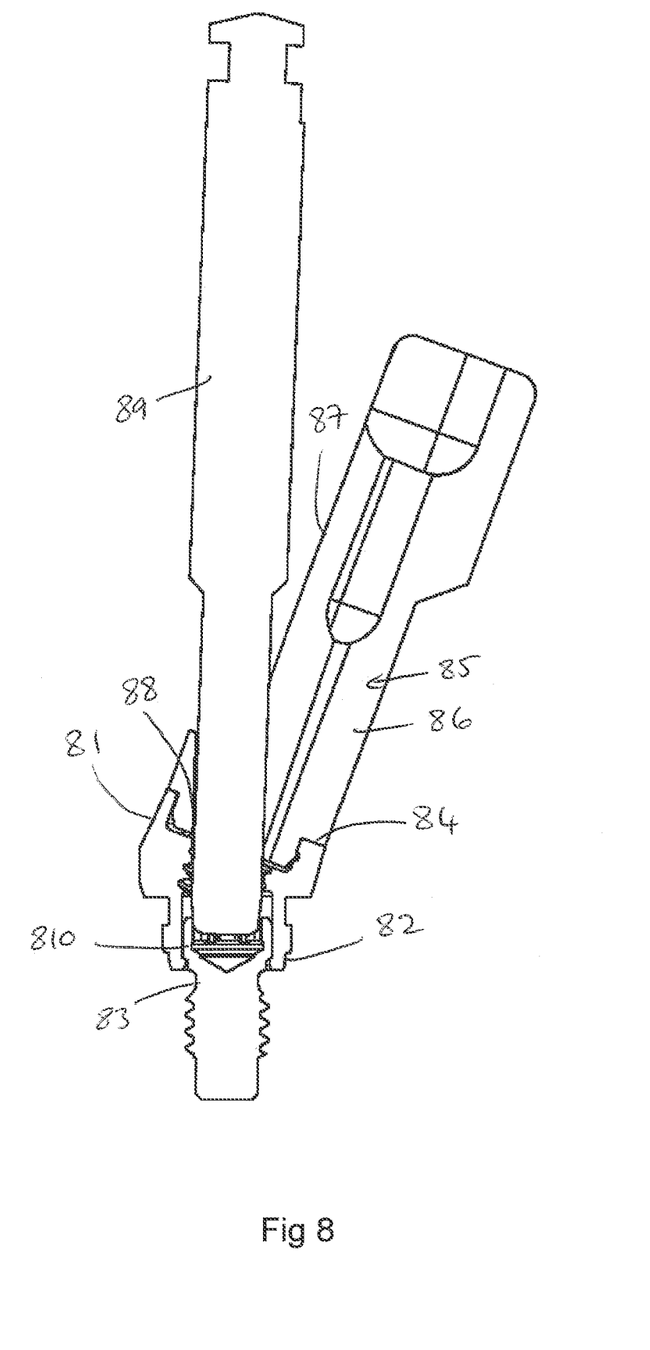
FIG. 8 shows a cross-sectional view of a spacer element fitted with a holder and with a screwdriver in place on the implant screw.

Referring to FIG. 8, there is shown a spacer element 81 provided with an integral locking ring 82. The locking ring is engaged with an implant screw 83. An upper surface 84 of the spacer element 81 is provided with a handle 85. The handle 85 comprises a longitudinal substantially cylindrical body 86, one side of which has a cut-away portion 87, such that, in situ, the cut-away portion 86 provides access to the bore(s) 88 of the spacer element 81. A screwdriver 89 can be passed through the cut-away portion to engage with the head 810 of the implant screw 83.

Figure 9A:
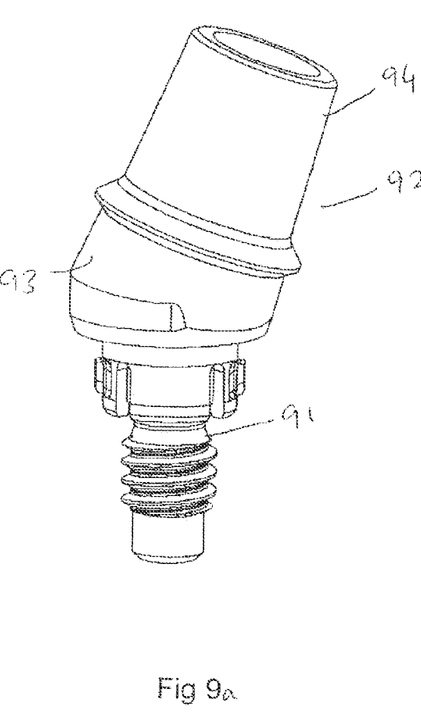
FIG. 9a shows a perspective view of an assembly that includes the spacer element of FIG. 3a attached to an implant screw and with an abutment fitted by means of an abutment screw.
Figure 9B:
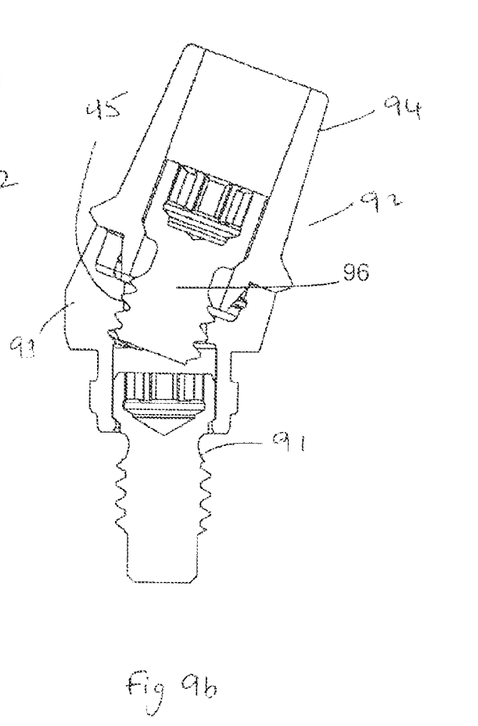

Referring to FIGS. 9a and 9b, once the implant (not shown) is in situ, a spacer 93 with a preferably pre-mounted implant screw 91 is placed into the implant through the support of the handle before the handle is removed. An impression is taken with an impression coping (not shown) and a healing abutment (not shown) is placed in the spacer 93. After tissue healing and the abutment 92 being incorporated into a dental construction, the construction is placed on the spacer 93 and fastened with the abutment screw 95. The construction can be made in a solid piece, for example in metal, ceramic or polymer, in such a way that it includes the abutment in order to provide access and space for the abutment screw 95 and a connection to the spacer 93. The abutment 92 comprises a collar 94 and an abutment screw 95. The abutment screw 95 is positioned inside the angulated threaded abutment screw bore 96.

The abutment screw 95 can be the same type as the implant screw 98 or different, for example, the thread can be of a wider diameter for the abutment screw 95 to allow provision of a larger screw access bore for better accessibility to the implant screw 91. The screwdriver connection 99a and 99b of the abutment screw 95 and implant screw 98 can be different or are preferably the same.

Figure 10:
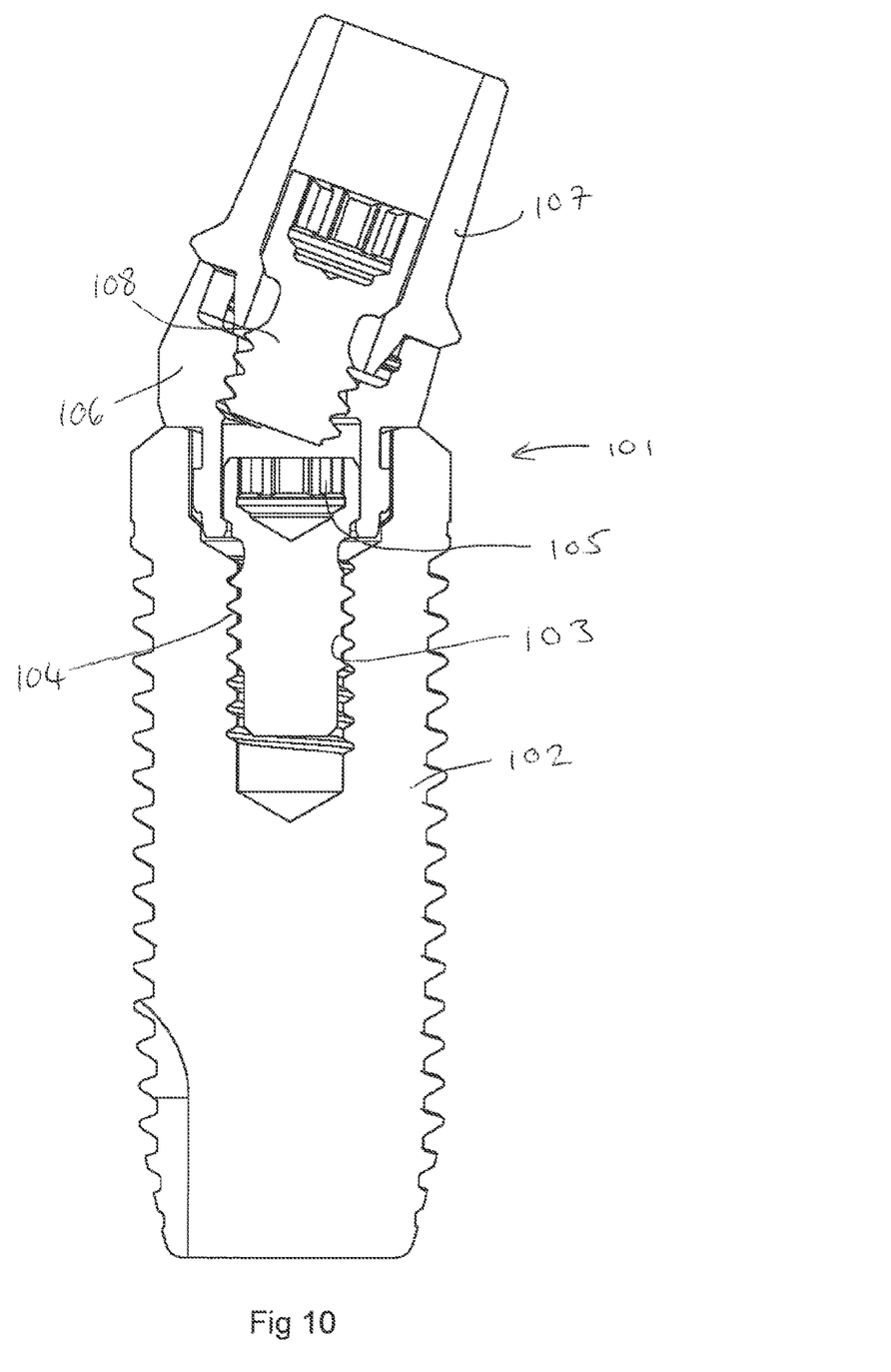
FIG. 10 shows a cross-sectional view of the assembly shown in FIG. 9a, including an implant.

Referring to FIG. 10, an implant assembly 101 includes an implant 102 and an implant screw 103 located in the implant 102. The implant screw 103 comprises a shaft portion 104 and a head 105, the head 105 being located within a spacer 106 substantially as described above. The spacer 106 is also connected to an abutment 107 by means of an abutment screw 108.

Figure 11:
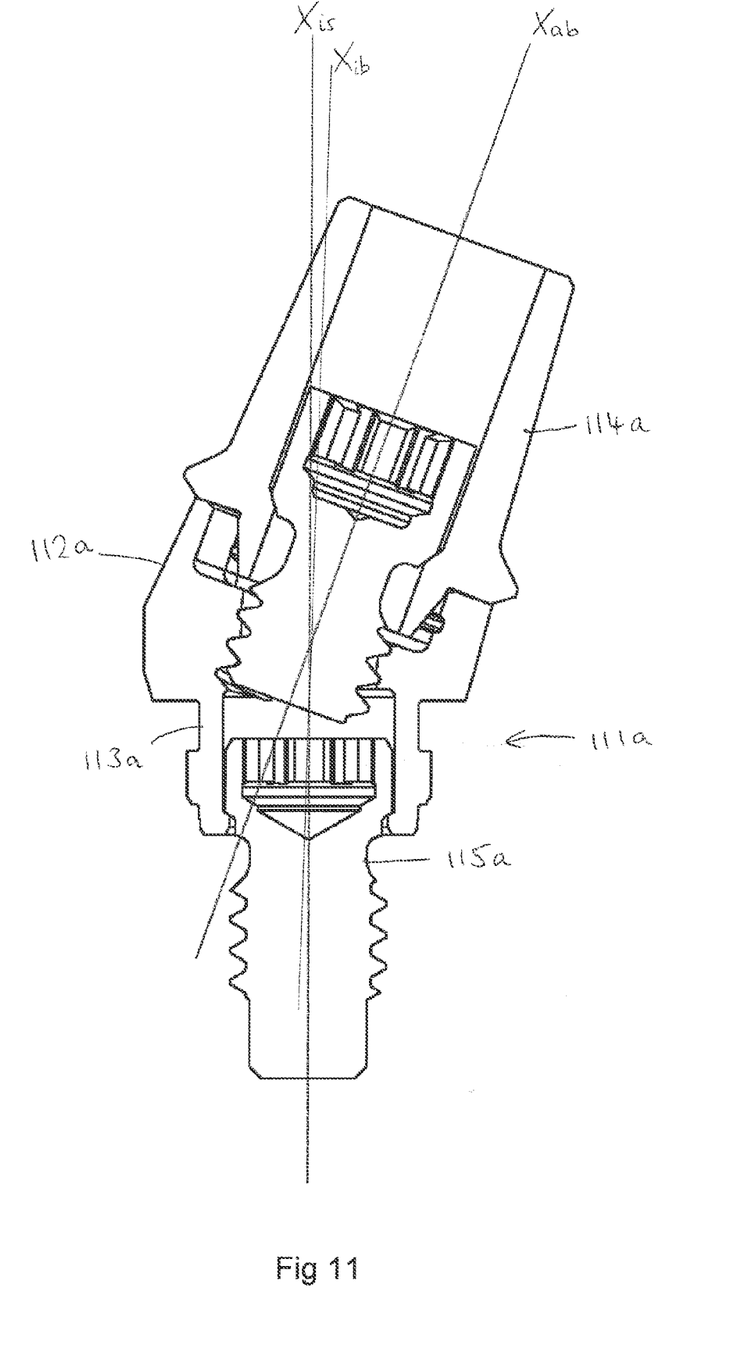
FIG. 11 shows a cross-sectional view of the assembly shown in FIG. 9a with the axes of the three bores indicated.

Referring to FIG. 11, an implant assembly 111a includes a spacer element 112a provided with a locking ring 113a and an abutment 114a located in the spacer element 112a. An implant screw 115a is located in the locking ring 113a. The lines show the longitudinal axes of the implant screw ($X_{is}$), the implant screw access bore ($X_{ib}$) and the abutment screw bore ($X_{ab}$). In FIG. 11, the longitudinal axes of the implant screw access bore ($X_{ib}$) and the abutment screw bore ($X_{ab}$) are shown intersecting at a point within the aperture of the spacer element 112a. It is not essential for these axes to intersect at such a point; they may be laterally offset from one another (e.g., into or out of the page, as illustrated). However, even in such a case, when the longitudinal axes of the implant screw access bore ($X_{ib}$) and the abutment screw bore ($X_{ab}$) are projected onto a plane extending substantially vertically through the aperture of the spacer element, the projected axes intersect.

Further structural modifications can be realised with respect to the exemplary embodiments described above.

The appended claims are incorporated by reference into the disclosure. All references, including publications, patent applications, and patents, cited herein are hereby incorporated by reference. The description or connotation, if any, of certain embodiments as "preferred" embodiments, and other recitation of embodiments, features, or ranged as being preferred, is not deemed to be limiting, and the invention is deemed to encompass embodiments that are presently deemed to be less preferred.

All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variation thereof is encompassed by the invention unless otherwise indicated herein or otherwise clearly contradicted by context. The description herein of any reference or patent or equipment, even if identified as "prior," is not intended to constitute a concession that such reference or patent is available as prior art against the present invention.

The invention claimed is:

1. A dental spacer element for use in a dental implant assembly, the dental spacer element comprising a single aperture therethrough, the single aperture further comprising a dental implant screw access bore and an offset dental abutment screw bore, wherein the single aperture is configured to receive a dental driving tool in a direction that is coaxial with a longitudinal axis of a dental implant screw, a locking ring is formed integrally with the dental spacer element, the locking ring including a plurality of longitudinal slots around a side wall of the locking ring, the longitudinal slots being open at a bottom end in a direction toward a threaded portion of the dental implant screw.

2. The dental spacer element as claimed in claim 1 wherein longitudinal axes of the dental implant screw access bore and the offset dental abutment screw bore, when projected, intersect within said single aperture.

3. The dental spacer element according to claim 1 wherein, in use, the dental implant screw access bore is inclined relative to the dental implant screw to which the dental spacer element is attached and a degree of incline is from 0 to 10 degrees.

4. The dental spacer element according to claim 1 wherein, in use, the dental implant screw access bore is substantially parallel to or coaxial with the longitudinal axis of the dental implant screw to which the dental spacer element is attached.

5. The dental spacer element according to claim 1 wherein the dental implant screw access bore is substantially threadless.

6. The dental spacer element according to claim 1 further comprising a dental implant engaging portion and/or a dental abutment screw engaging portion.

7. The dental spacer element according to claim 1 wherein the dental abutment screw bore is offset or inclined from the dental implant screw access bore.

8. The dental spacer element according to claim 7 wherein the dental abutment screw bore is offset or inclined from the dental implant screw access bore at an angle in a range 1 to 30 degrees.

9. The dental spacer element according to claim 1 wherein, in use, the dental spacer element is intermediate a dental abutment and a dental implant or the dental implant screw and an angle between longitudinal axes of the dental abutment and the dental implant or the dental implant screw is in a range of 10 to 40 degrees.

10. The dental spacer element according to claim 1 wherein the dental abutment screw bore is or is partially provided with an internal screw thread.

11. A dental spacer element for use in a dental implant assembly, the dental spacer element comprising a single aperture therethrough, the single aperture further comprising a threadless bore and an offset but overlapping threaded bore, wherein the single aperture is configured to receive a dental driving tool in a direction that is coaxial with a longitudinal axis of a dental implant screw of the dental implant assembly, a locking ring is formed integrally with the dental spacer element, the locking ring including a plurality of longitudinal slots around a side wall of the locking ring, the longitudinal slots being open at a bottom end in a direction toward a threaded portion of the dental implant screw.

12. The dental spacer element according to claim 11 wherein, in use, the threadless bore is inclined relative to the dental implant screw to which the dental spacer element is attached and a degree of incline of the threadless bore relative to the dental implant screw is from 0 to 10 degrees.

13. The dental spacer element according to claim 12, wherein the threadless bore is substantially coaxial with the dental implant screw.

14. A dental spacer element for use in a dental implant assembly, the dental spacer element comprising a single aperture therethrough, the aperture further comprising a threadless bore and an offset but non-overlapping threaded bore, wherein the aperture is configured to receive a dental driving tool in a direction that is coaxial with a longitudinal axis of a dental implant screw, a locking ring is formed integrally with the dental spacer element, the locking ring including a plurality of longitudinal slots around a side wall of the locking ring, the longitudinal slots being open at a bottom end in a direction toward a threaded portion of the dental implant screw.

15. A dental spacer element comprising a single aperture therethrough, the single aperture comprising a dental implant screw access bore and an offset dental abutment screw bore, or a threadless bore and an offset threaded bore that is overlapping or non-overlapping with the threadless bore, wherein the dental spacer element is provided with means for engaging a dental abutment screw, wherein the single aperture is configured to receive a dental driving tool in a direction that is coaxial with a longitudinal axis of a dental implant screw, the dental spacer element further comprising a dental implant screw engaging portion that engages with the dental implant screw, and a locking ring is formed integrally with the dental spacer element, the locking ring including a plurality of longitudinal slots around a side wall of the locking ring, the longitudinal slots being open at a bottom end in a direction toward a threaded portion of the dental implant screw.

16. A dental implant assembly comprising a dental spacer element including a single aperture therethrough, the single aperture comprising a dental implant screw access bore and a dental offset abutment screw bore, or a threadless bore and an offset threaded bore that is overlapping or non-overlapping with the threadless bore, wherein the dental spacer element is provided with means for engaging a dental abutment screw, and one or more of a dental implant, a dental abutment or a dental bridge, where the dental spacer element includes a dental implant screw engaging portion that engages with a dental implant screw, a locking ring is formed integrally with the dental spacer element, the locking ring including a plurality of longitudinal slots around a side wall of the locking ring, the longitudinal slots being open at a bottom end in a direction toward a threaded portion of the dental implant screw, and wherein the single aperture is configured to receive a dental driving tool in a direction that is coaxial with a longitudinal axis of the dental implant screw.

17. The dental implant assembly according to claim 16 including the dental implant screw and the dental abutment screw.

18. A dental implant assembly kit comprising a dental spacer element including a single aperture therethrough, the single aperture comprising a dental implant screw access bore and an offset dental abutment screw bore, or a threadless bore and an offset threaded bore that is overlapping or non-overlapping with the threadless bore, wherein the dental spacer element is provided with means for engaging a dental abutment screw, and means for engaging one or more of a dental driving tool, a dental implant and a dental abutment, wherein a locking ring is formed integrally with the dental spacer element, wherein the single aperture is configured to receive the dental driving tool in a direction that is coaxial with a longitudinal axis of a dental implant screw, and wherein the locking ring includes a plurality of longitudinal slots around a side wall of the locking ring, the longitudinal slots being open at a bottom end in a direction toward a threaded portion of the dental implant screw.

19. The dental implant assembly kit according to claim 18 wherein the kit includes one or more of the dental implant screw and the dental abutment screw.

20. A method of producing a dental implant assembly including steps of:
providing a dental spacer element including a single aperture therethrough, the single aperture comprising a dental implant screw access bore and an offset dental abutment screw bore, or a threadless bore and an offset threaded bore that is overlapping or non-overlapping with the threadless bore, wherein the dental spacer element is provided with a dental implant screw engaging portion that engages with a dental implant screw and means for engaging a dental abutment screw, and a locking ring is formed integrally with the dental spacer element, the locking ring including a plurality of longitudinal slots around a side wall of the locking ring, the longitudinal slots being open at a bottom end in a direction toward a threaded portion of the dental implant screw;
locating said dental spacer element on the dental implant screw;
locating a dental abutment in the dental spacer element; and
inserting a dental driving tool into the single aperture in a direction coaxial with the dental implant screw.

21. A method of anchoring a dental abutment including:
equipping a dental spacer element with a dental implant screw, the dental spacer element comprising a single aperture therethrough, the single aperture further comprising a dental implant screw access bore and an offset dental abutment screw bore, or a threadless bore and an offset threaded bore that is overlapping or non-overlapping with the threadless bore, and the dental spacer element including a locking ring formed integrally therewith, the locking ring including a plurality of longitudinal slots around a side wall of the locking ring, the longitudinal slots being open at a bottom end in a direction toward a threaded portion of the dental implant screw;
positioning said dental spacer element on a dental implant;
locating a dental abutment in the dental spacer element; and
inserting a dental driving tool into the single aperture in a direction coaxial with the dental implant screw.

22. A dental construction or dental bridge including a dental spacer element comprising a single aperture therethrough, the single aperture comprising a dental implant screw access bore and an offset dental abutment screw bore, or a threadless bore and an offset threaded bore that is overlapping or non-overlapping with the threadless bore, wherein the dental spacer element is provided with a dental implant screw engaging portion that engages with a dental implant screw and means for engaging a dental abutment screw, a locking ring is formed integrally with the dental spacer element, the locking ring including a plurality of longitudinal slots around a side wall of the locking ring, the longitudinal slots being open at a bottom end in a direction toward a threaded portion of the dental implant screw, and wherein the single aperture is configured to receive a dental driving tool in a direction that is coaxial with a longitudinal axis of the dental implant screw.

23. A dental spacer element comprising a single aperture therethrough, the single aperture comprising a dental implant screw access bore and an offset dental abutment screw bore, or a threadless bore and an offset threaded bore that is overlapping or non-overlapping with the threadless bore, and wherein the dental spacer element is provided with a dental implant screw engaging portion that engages with a dental implant screw and means for engaging a dental abutment screw, wherein at least a portion of the single aperture includes a connection portion for a handle to be attached for carrying and positioning the dental spacer element to a dental implant, a locking ring is formed integrally with the dental spacer element, the locking ring including a plurality of longitudinal slots around a side wall of the locking ring, the longitudinal slots being open at a bottom end in a direction toward a threaded portion of the dental implant screw, and wherein the single aperture is configured to receive a dental driving tool in a direction that is coaxial with a longitudinal axis of the dental implant screw.

24. A dental spacer element comprising a single aperture therethrough, the single aperture comprising a dental implant screw access bore and an offset dental abutment screw bore, or a threadless bore and an offset threaded bore that is overlapping or non-overlapping with the threadless bore, wherein at least an opening of the single aperture is substantially circular with a notch or cut-away portion extending toward an outer wall of the dental spacer element to facilitate insertion of a substantially linear dental driving tool therein in a direction that is coaxial with a longitudinal axis of a dental implant screw, a distance from a center of the opening to a perimeter of the opening at the notch or cut-away portion of the opening being longer than a distance from the center of the opening to the perimeter of the opening at another portion of the opening, and a locking ring is formed integrally with the dental spacer element, the locking ring including a plurality of longitudinal slots around a side wall of the locking ring, the longitudinal slots being open at a bottom end in a direction toward a threaded portion of the dental implant screw.

* * * * *